United States Patent
Otsubo et al.

(10) Patent No.: US 7,217,261 B2
(45) Date of Patent: May 15, 2007

(54) PULL-ON DISPOSABLE WEARING ARTICLE

(75) Inventors: Toshifumi Otsubo, Kagawa-ken (JP); Shunsuke Takino, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 0 days.

(21) Appl. No.: 11/046,863

(22) Filed: Feb. 1, 2005

(65) Prior Publication Data
US 2005/0131374 A1      Jun. 16, 2005

Related U.S. Application Data

(63) Continuation of application No. PCT/JP03/10313, filed on Aug. 13, 2003.

(30) Foreign Application Priority Data
Aug. 30, 2002    (JP)    ............... 2002-253992

(51) Int. Cl.
*A61F 13/15* (2006.01)
(52) U.S. Cl. .................. 604/385.29; 604/361
(58) Field of Classification Search ................ 604/361, 604/385.01–385.3
See application file for complete search history.

(56) References Cited

U.S. PATENT DOCUMENTS

| | | | |
|---|---|---|---|
| 5,171,239 A * | 12/1992 | Igaue et al. ............ | 604/385.29 |
| 5,415,649 A | 5/1995 | Watanabe et al. | |
| 5,575,783 A | 11/1996 | Clear et al. | |
| 5,745,922 A | 5/1998 | Rajala et al. | |
| 5,846,232 A | 12/1998 | Serbiak et al. | |
| 6,049,916 A | 4/2000 | Rajala et al. | |

(Continued)

FOREIGN PATENT DOCUMENTS

EP      0761194      8/1996

(Continued)

OTHER PUBLICATIONS

Patent Abstract of Japan; Publication No. 2002-095692 published Apr. 2, 2002 w/Japanese Application No. 2000-290745 filed Sep. 25, 2000.

(Continued)

*Primary Examiner*—Tatyana Zalukaeva
*Assistant Examiner*—Ginger Chapman
(74) *Attorney, Agent, or Firm*—Lowe Hauptman & Berner LLP (57) ABSTRACT

An article includes an auxiliary elastic member extending in a waist-circumferential direction and arranged between a waist-surrounding elastic member extending in front and rear waist regions and leg-holes of a base sheet assembly in a stretched state. The base sheet assembly includes a first sheet and a second sheet. The auxiliary elastic member includes first elastic elements and second elastic elements. In the article, the first and second elastic elements respectively have longitudinally opposite end portions, middle portions and the remaining portions. The end portions of the first and second elastic elements are secured to the first and second sheet, the middle portions of the first elastic elements are secured to the second sheet and the remaining portions of the first and second elastic elements as well as the middle portions of the second elastic elements are let free from the first and second sheets.

8 Claims, 7 Drawing Sheets

U.S. PATENT DOCUMENTS

| | | |
|---|---|---|
| 6,297,424 B1 * | 10/2001 | Olson et al. .......... 604/361 |
| 6,595,976 B2 | 7/2003 | Jitoe et al. |
| 6,923,797 B2 | 8/2005 | Shinohara et al. |
| 2002/0049421 A1 | 4/2002 | Hayase et al. |

FOREIGN PATENT DOCUMENTS

| | | |
|---|---|---|
| EP | 0762293 | 8/1996 |
| EP | 0 761 193 | 3/1997 |
| EP | 0990434 | 4/2000 |
| EP | 1157681 | 11/2001 |
| EP | 1184012 | 3/2002 |
| EP | 1197195 | 4/2002 |
| JP | 08-084747 | 4/1996 |
| JP | 1997-38134 | 2/1997 |
| JP | 09-056747 | 3/1997 |
| JP | 09-099006 | 4/1997 |
| JP | 11-299829 | 11/1999 |
| JP | 2000-107225 | 4/2000 |
| JP | 2001-145666 | 5/2001 |
| JP | 2001-157690 | 6/2001 |
| JP | 2001-231078 | 8/2001 |
| JP | 2002-095692 | 4/2002 |
| JP | 2003-038556 | 2/2003 |

OTHER PUBLICATIONS

Patent Abstract of Japan; Publication No. 2001-145666 published May 29, 2001 w/Japanese Application No. 11-329189 filed Nov. 19, 1999.

Patent Abstract of Japan; Publication No. 08-084747 published Apr. 2, 2002 w/Japanese Application No. 06-246732 filed Sep. 16, 2004.

Patent Abstract of Japan; Publication No. 08-084747 published Apr. 2, 2000 w/Japanese Application No. 07-221976 filed Aug. 30, 1995.

* cited by examiner

PULL-ON DISPOSABLE WEARING ARTICLE

BACKGROUND OF THE INVENTION

The present invention relates to a pull-on disposable wearing article for absorption and containment of bodily discharges.

Japanese Patent Application Publication No. 2000-107225A discloses a pull-on disposable diaper comprising a liquid-pervious topsheet, a liquid-impervious backsheet and a liquid-absorbent core interposed between these top- and backsheets in which front and rear waist regions are joined to each other in the vicinity of lateral marginal zones of these waist regions to obtain a pants-shape having a waist-hole and a pair of leg-holes. This pull-on disposable diaper further comprises a plurality of waist-surrounding elastic members attached to a peripheral edge zone of the waist-hole so that the waist-surrounding elastic members may contract in a waist-circumferential direction, a plurality of leg-surrounding elastic members attached to peripheral zones of the respective leg-holes so that the leg-surrounding elastic members may contract in a leg-circumferential direction and a plurality of auxiliary elastic members attached to the waist regions between the waist-surrounding elastic member and the leg-surrounding elastic members so that the auxiliary elastic members may contract in the waist-circumferential direction.

The auxiliary elastic members are arranged in the front waist region so as to be spaced apart from one another by regular dimensions in a longitudinal direction and having longitudinal opposite end portions lying in the vicinity of the lateral marginal zones of the front waist region and middle portions lying between the end portions and extending across the core. Longitudinally opposite end portions of the waist-surrounding elastic member are interposed between the top- and backsheet and secured to these sheets. The middle portions of the auxiliary elastic member are secured neither to the backsheet nor to the core, i.e., let free from the backsheet and the core. Such arrangement is effective to protect the region of the backsheet in which the middle portion of the auxiliary elastic member lies from formation of gathers and to ensure a smooth touch of the backsheet even when the auxiliary elastic members contract in the waist-circumferential direction.

In the diaper disclosed in the above-cited Publication, there is an anxiety that movement of the wearer's waist transmitted to the auxiliary elastic member extending in the front waist region may cause the middle portion of the auxiliary elastic member to shift in the longitudinal direction and, in consequence, the auxiliary elastic member to locally gather together. The auxiliary elastic member locally gathering together in this manner may form a bundle, so a stretch stress of the auxiliary elastic member may increase and uncomfortably tighten the wearer's waist. The auxiliary elastic member locally gathering together may hinder a contractile force of the auxiliary elastic member from being utilized to press the entire area of the core against the wearer's waist and sometimes deteriorate a bodily discharge absorbing capacity expected for the part of the core lying in the front waist region.

SUMMARY OF THE INVENTION

It is an object of the present invention to provide a pull-on disposable wearing article free from the anxiety that auxiliary elastic members might locally gather together and enables a bodily discharge absorbing capacity expected for the part of a liquid-absorbent panel lying in a front waist region to be fully utilized.

According to the present invention, there is provided a pull-on disposable wearing article generally comprising a base sheet assembly defining front and rear waist regions and a crotch region extending between the waist regions and a liquid-absorbent panel attached to an inner side of the base sheet assembly so as to extend over the crotch region further into the front and rear waist regions, the front and rear waist regions defined by the base sheet assembly being connected to each other in vicinities of lateral marginal zones of the base sheet assembly to form a waist-hole and a pair of leg-holes, the base sheet assembly being provided with a waist-surrounding elastic member extending in a waist-circumferential direction attached in stretched state thereto along a peripheral edge of the waist-hole in the front and rear waist regions and with auxiliary elastic members extending in the waist-circumferential direction and attached in a stretched stated to the base sheet assembly so as to be spaced apart from one another by regular dimensions in a longitudinal direction between the waist-surrounding elastic member and the leg-holes at least in the front waist regions of the front and rear waist regions defined by the base sheet assembly.

The present invention further comprises the base sheet assembly comprising a first sheet facing the panel and a second sheet facing away from the panel, the auxiliary elastic members comprising first elastic elements lying below the waist-surrounding elastic member and interposed between the first and second sheets and second elastic elements lying below the first elastic elements and interposed between the first and second sheets, the first and second elastic elements respectively having longitudinally opposite end portions extending in vicinities of the lateral marginal zones of the base sheet assembly, middle portions extending across the panel and the remaining portions lying outside transversely opposite side edge zones of the panel and extending between respective the end portions and the middle portions and the longitudinally opposite end portions of the first and second elastic elements and the middle portions of the first elastic elements are secured to at least one of the first and second sheets while the remaining portions of the first and second elastic elements and the middle portions of the second elastic elements being let free from both the first sheet and the second sheet.

The present invention includes the following embodiments. Indication sheets each having a given indicator element thereon are placed in regions in which the middle portions of the second elastic elements extend and secured to an inner surface of the second sheet.

Heat-sealing spots serving to join the first and second sheets are distributed in regions in which the remaining portions of the first and second elastic elements lie so that the individual heat-sealing spots are located between each pair of the first elastic elements adjacent to each other as well as between each pair of the second elastic elements adjacent to each other.

The heat-sealing spots are arranged along the transversely opposite side zones of the panel extending in the front and rear waist regions.

Leg-surrounding elastic members are attached in a stretched state to the base sheet assembly along peripheral edges of respective the leg-holes.

The panel comprises a liquid-pervious upper sheet facing a wearer's body, a liquid-impervious lower sheet facing away from the wearer's body and a liquid-absorbent core interposed between the upper and lower sheets.

DETAILED DESCRIPTION OF THE PREFERRED EMBODIMENTS

Detail of a pull-on disposable wearing article according to the present invention will be more fully understood from the description given hereunder with reference to the accompanying drawings.

Figure 1:
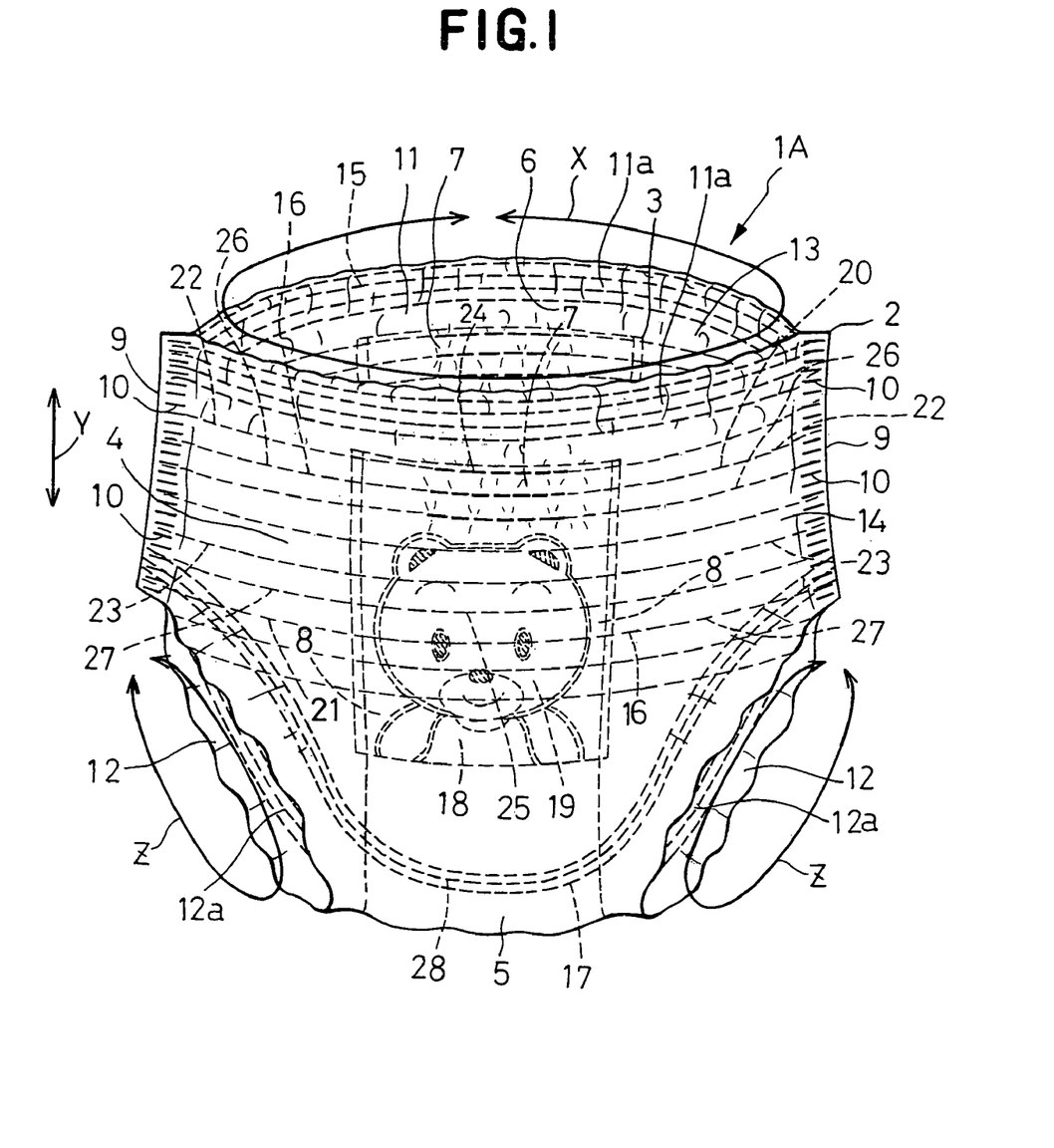
FIG. 1 is a perspective view showing an example of a wearing article.
Figure 2:
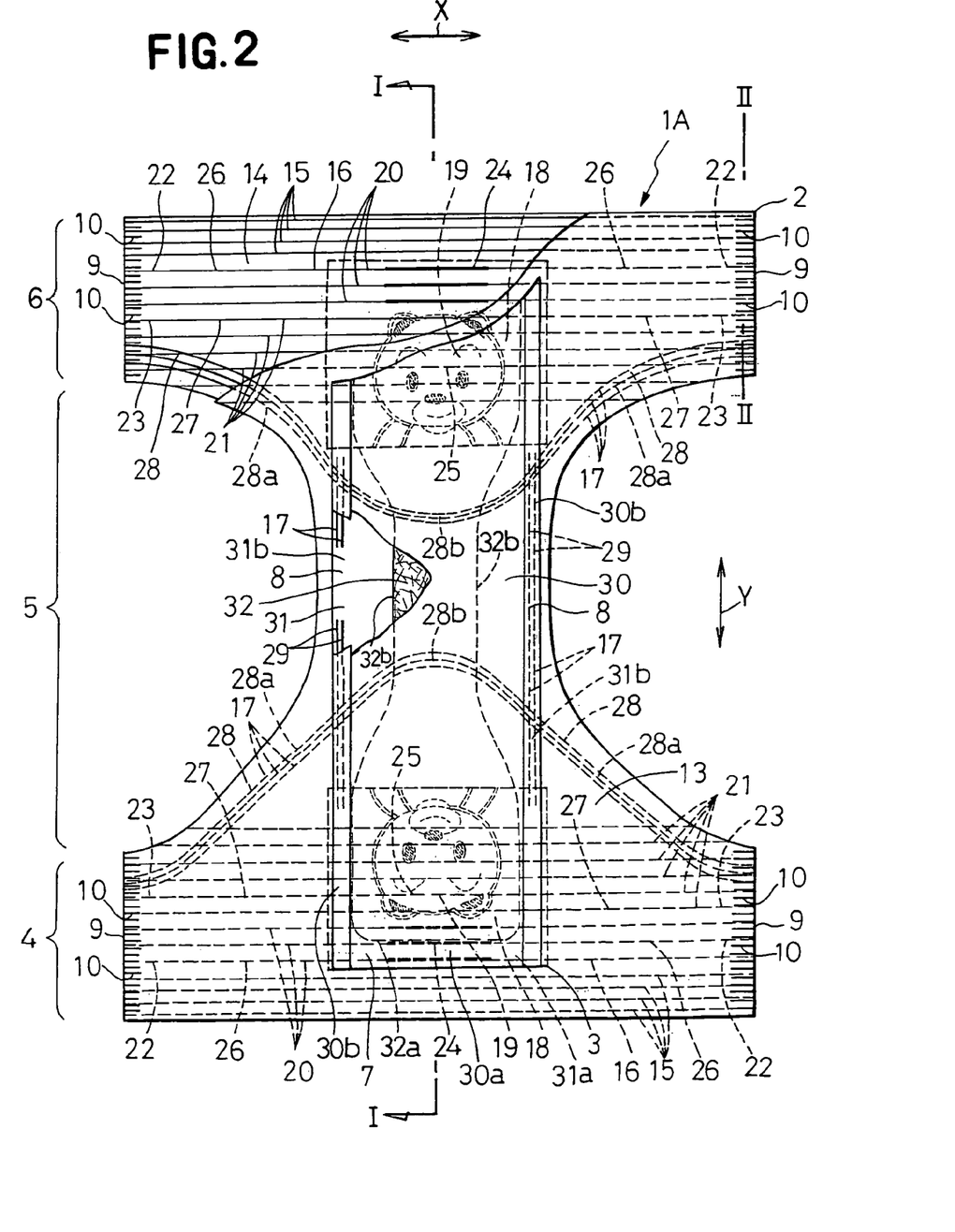
FIG. 2 is a partially cutaway developed plan view showing the article of FIG. 1 with the front and rear waist regions disconnected from each other.
Figure 3:
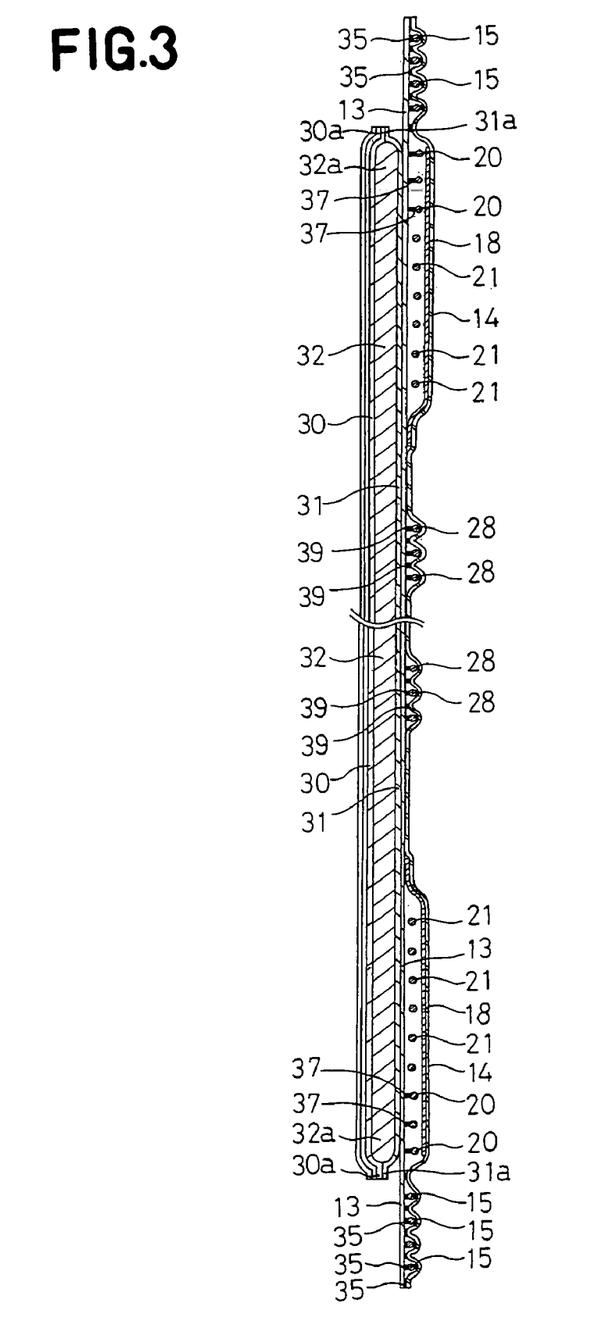
FIG. 3 is a sectional view taken along a line I—I in FIG. 2.
Figure 4:
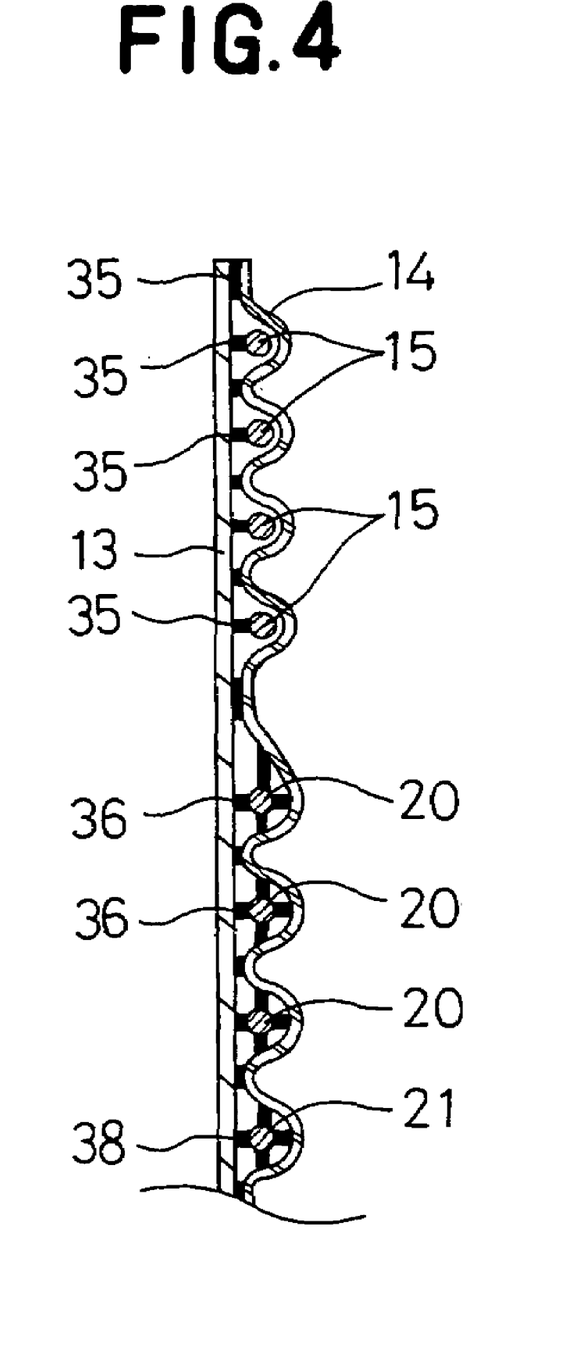
FIG. 4 is a sectional view taken along a line II—II in FIG. 2.

FIG. 1 is a perspective view showing a pull-on wearing article 1A according to a typical embodiment of the invention, FIG. 2 is a partially cutaway developed plan view showing the article 1A of FIG. 1 with front and rear waist regions 4, 6 disconnected from each other, FIG. 3 is a sectional view taken along a line I—I in FIG. 2 and FIG. 4 is a sectional view taken along a line II—II in FIG. 2. In FIGS. 1 and 2, a waist-circumferential direction is indicated by an arrow X, a longitudinal direction is indicated by an arrow Y and a leg-circumferential direction is indicated by an arrow Z (in FIG. 1 alone). Expression "inner surfaces of inner and outer sheets 13, 14 (corresponding to first and second sheets), an indication sheet 18 and upper and lower sheets 30, 31" should be understood to be surfaces facing a core 32 and expression "outer surfaces of these sheets 13, 14, 18, 30, 31" should be understood to be surfaces to be surfaces of these sheets facing away from the core 32.

The article 1A comprises a base sheet assembly 2 and a liquid-absorbent panel 3 attached to an inner side of the base sheet assembly 2. The base sheet assembly 2 is composed of front and rear waist regions 4, 6 opposed to each other and a crotch region 5 extending between these waist regions 4, 6. The panel 3 extends between the front and rear waist regions 4, 6 of the base sheet assembly 2 and has a pair of longitudinally opposite end zones 7 lying in the front and rear waist regions 4, 6 of the base sheet assembly 2, respectively, so as to extend in the waist-circumferential direction and a pair of transversely opposite side zones 8 extending between the front and rear waist regions 4, 6 of the base sheet assembly 2 in the longitudinal direction.

The front and rear waist regions 4, 6 defined by the base sheet assembly 2 are overlaid and joined together in the vicinity of the lateral marginal zones 9 of the base sheet assembly 2 extending outward beyond the side zones 8 of the panel 3 by means of a plurality of heat-sealing lines 10 arranged intermittently in the longitudinal direction. The article 1A is in the form of pants having a waist-hole 11 and a pair of leg-holes 12. The crotch region 5 describes circular arcs which are convex inward in the waist-circumferential direction of the article 1A. The base sheet assembly 2 has a generally hourglass-like planar shape as will be seen in FIG. 2.

The base sheet assembly 2 comprises an inner sheet 13 (first sheet) facing the panel 3 and an outer sheet 14 (second sheet) facing away from the panel 3, i.e., lying outside the inner sheet 13. The inner sheet 13 and the outer sheet 14 are made of hydrophobic fibrous nonwoven fabric. Along a peripheral zone 11a of the waist-hole 11 defined by the end zones 7 of the front and rear waist regions 4, 6, respectively, the base sheet assembly 2 is provided with waist-surrounding elastic members 15 attached thereto in a stretched state. In the front and rear waist regions 4, 6, the base sheet assembly 2 is further provided between the waist-surrounding elastic member 15 and the leg-holes 12 with auxiliary elastic members 16 attached thereto and spaced apart from one another by given dimensions in the longitudinal direction. Along peripheral zones 12a of the leg-holes 12 defined in the crotch region 5, the base sheet assembly 2 is provided with respective leg-surrounding elastic members 17 attached thereto in a stretched state. In the front and rear waist regions 4, 6, the base sheet assembly 2 is provided with indication sheets 18, respectively.

The waist-surrounding elastic members 15 are interposed between the inner sheet 13 and the outer sheet 14 and attached to these sheets 13, 14 by means of a hot melt adhesive 35. The auxiliary elastic members 16 include a plurality of first elastic elements 20 lying below the waist-surrounding elastic member 15 and a plurality of second elastic elements 21 lying below these first elastic elements 20. The first and second elastic elements 20, 21 are interposed between the inner sheet 13 and the outer sheet 14.

The first and second elastic elements 20, 21 respectively have opposite end portions 22, 23 extending in the vicinity of the lateral marginal zones 9 of the base sheet assembly 2, middle portions 24, 25 extending across the panel 3 and the remaining portions 26, 27 lying outside the opposite side zones 8 of the panel 3 so as to extend between the end portions 22, 23 and the middle portions 24, 25. The middle portions 24 of the first elastic elements 20 extend along the opposite end zones 7 of the panel 3.

The end portions 22 of the first elastic elements 20 are secured to an outer surface of the inner sheet 13 and to an inner surface of the outer sheet 14 by means of a hot melt adhesive 36. The middle portions 24 of the first elastic elements 20 are secured, in the front and rear waist regions 4, 6, to the outer surface of the inner sheet 13 by means of a hot melt adhesive 37. The remaining portions 26 of the first elastic elements 20 are not secured to these inner and outer sheets 13, 14 and let free from these sheets 13, 14. It should be understood that the end portions 22 and the middle portions 24 of the first elastic elements 20 may be secured to at least one of the inner and outer sheets 13, 14.

The end portions 23 of the second elastic elements 21 are secured to the outer surface of the inner sheet 13 and to the inner surface of the outer sheet 14 by means of a hot melt adhesive 38. The middle portions 25 and the remaining portions 27 of the second elastic elements 21 are not secured to the inner and outer sheets 13, 14 and let free from these sheets 13, 14. It should be understood that the end portions 23 of the second elastic elements 21 may be secured to at least one of the inner and outer sheets 13, 14.

Each of the indication sheets 18 is interposed between the inner and outer sheets 13, 14 and has its outer surface joined to the inner surface of the outer sheet 14 by means of a hot melt adhesive (not shown). As a stock material for this indication sheet 18, a breathable but liquid-impervious plastic film is used. The indication sheet 18 is printed on its outer surface with an indicator element 19 in the form of illustrated bear's head.

The leg-surrounding elastic members 17 include third elastic elements 28 attached to the base sheet assembly 2 and fourth elastic elements 29 attached to the panel 3. The third elastic elements 28 are interposed between the inner and outer sheets 13, 14 and attached to these sheets 13, 14 by means of a hot melt adhesive 39 intermittently applied to these sheets 13, 14, respectively. The third elastic elements 28 describe a curve which is convex toward a central zone of the crotch region 5 from the front and rear waist regions 4, 6. The third elastic elements 28 have lateral portions 28a extending along the peripheral edges of the leg-holes 12 in the let-circumferential direction and middle portions 28b extending cross the central zone of the crotch region 5.

The panel 3 has a rectangular shape which is relatively long in the longitudinal direction and comprises a liquid-pervious upper sheet 30 facing the wearer's body, a liquid-impervious lower sheet 31 facing away from the wearer's body and a liquid-absorbent core 32 interposed between these sheets 30, 31. The panel 3 has the end zones 7 lying inside the longitudinally opposite end portions of the base sheet assembly 2. In the panel 3, the lower sheet 31 has its outer surface intermittently joined to the inner surface of the inner sheet 13 by means of a hot melt adhesive (not shown). Alternatively, an outer surface of the lower sheet 31 may be joined to the inner surface of the inner sheet 13 only along the longitudinally opposite end zones 7 of the panel 3 and the remaining zone of the panel 3 may be let free from the inner sheet 13.

The upper and lower sheets 30, 31 respectively have longitudinally opposite end zones 30a, 31a extending outward beyond longitudinally opposite ends 32a of the core 32 in the longitudinal direction and lateral marginal zones 30b, 31b extending outward beyond transversely opposite side edges 32b of the core 32 in the waist-circumferential direction. Along the end zones 30a, 31a and the lateral marginal zones 30b, 31b, the upper and lower sheets 30, 31 respectively have inner surfaces overlaid and joined together. In the front and rear waist regions 4, 6, the lateral marginal zones 30b, 31b of the upper and lower sheets 30, 31 are folded inward in the waist-circumferential direction of the article 1A. In the front and rear waist regions 4, 6, the lateral marginal zones 30b, 31b of the upper and lower sheets 30, 31 are thus collapsed in ward in the waist-circumferential direction of the article 1A with the outer surface of the upper sheet 30 overlaid and joined to itself in a collapsed state. The fourth elastic elements 29 are interposed between the upper and lower sheets 30, 31 and attached to the inner surfaces of these sheets 30, 31 along the lateral marginal zones 30b, 31b.

In the article 1A, the lateral portions 28a of the third elastic elements 28 constituting the leg-surrounding elastic member 17 intersect the fourth elastic elements 29 constituting the leg-surrounding elastic member 17 so that these third and fourth elastic elements 28, 29 define together generally annular curves along the peripheral edges of the respective leg-holes 12. In the article 1A, these elastic elements 28, 29 cooperate with one another to tighten the wearer' thighs.

In the article 1A, the middle portions 24 of the first elastic elements 20 are secured to the inner sheet 13 in the front and rear waist regions 4, 6. Therefore, it is not likely that the middle portions 24 of the first elastic elements 20 might shift in the longitudinal direction and these first elastic elements 20 might locally gather together in the front and rear waist regions 4, 6 even if movement of the wearer's waist or hip is transmitted to the first elastic elements 20. In the article 1A, it is also not likely that the first elastic elements 20 might form one or more bundles tending to locally tighten the wearer's waist or hip.

In the article 1A, there is no anxiety that the middle portions 24 of the first elastic elements 20 might be separated off from the end zones 7 of the panel 3. Instead, the middle portions 24 of the first elastic elements 20 function to force the end zones 7 of the panel 3 against the wearer's waist or hip as the first elastic elements 20 contract inward in the waist-surrounding direction. In this way, there is no anxiety that the bodily discharge absorbing capacity of the panel 3 might be deteriorated in the vicinity of its end zones 7 lying in the front and rear waist regions 4, 6.

In the article 1A, the remaining portions 26, 27 of the first and second elastic elements 20, 21 as well as the middle portions 25 of the second elastic elements 21 are not secured to the inner and outer sheets 13, 14. Such a unique arrangement can reliably avoid an anxiety that the region of the base sheet assembly 2 in which the remaining portions 26 and the middle portions 25 lie might be formed with a plurality of gathers. In this way, touch and appearance of the base sheet assembly 2 can be improved. Furthermore, placement of the indication sheets 18 in these regions occupied by the middle portions 25 of the second elastic elements 21 ensures that not only the base sheet assembly 2 but also the indication sheets 18 are free from formation of the gathers. Consequently, it is not likely that the indicator elements 19 printed thereon might become unclear.

Figure 5:
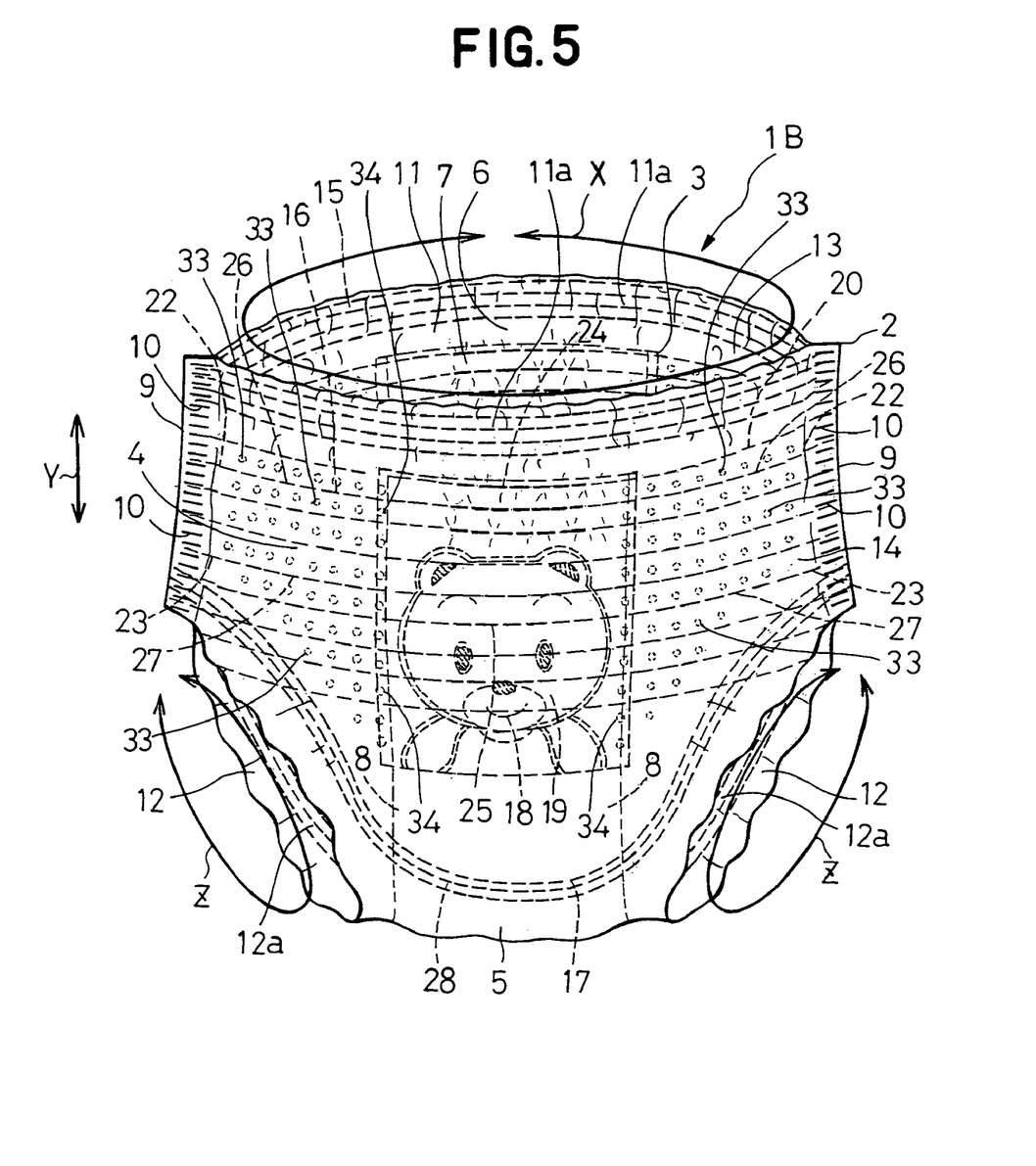
FIG. 5 is a perspective view showing another example of the wearing article.
Figure 6:
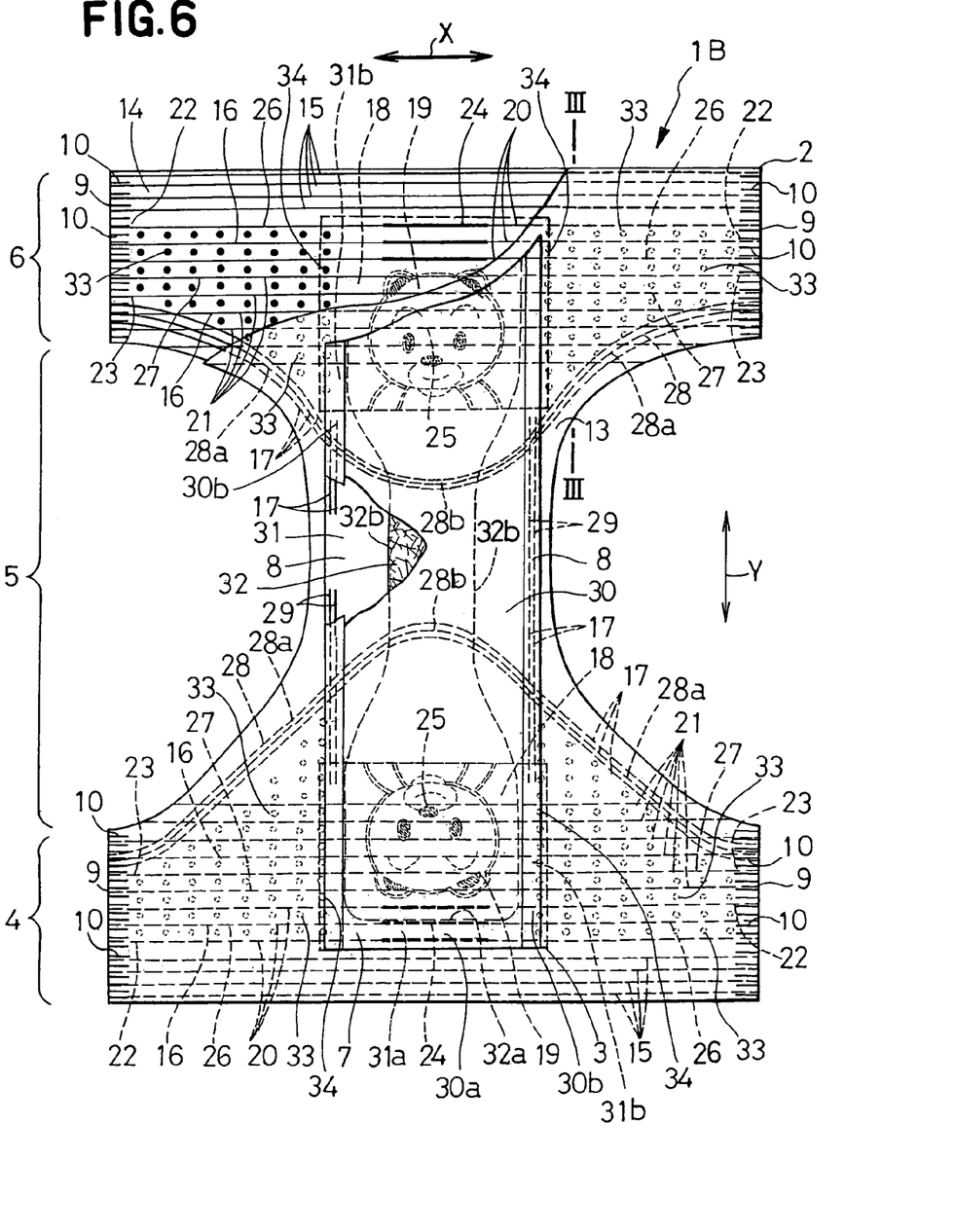
FIG. 6 is a partially cutaway developed plan view showing the article of FIG. 5 with the front and rear waist regions being disconnected from each other.
Figure 7:
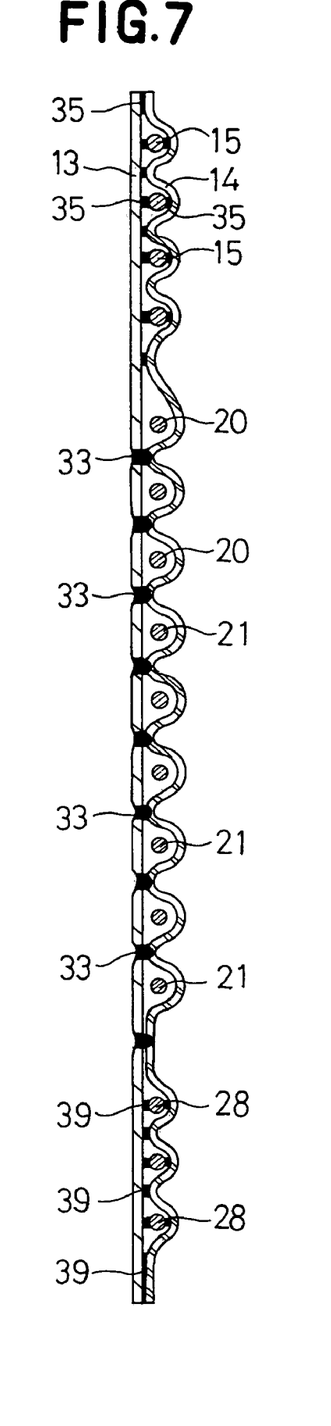
FIG. 7 is a sectional view taken along a line III—III in FIG. 6.

FIG. 5 is a perspective view showing the wearing article 1B according to another embodiment of the invention, FIG. 6 is a partially cutaway developed plan view showing the article 1B of FIG. 5 with the front and rear waist regions being disconnected from each other and FIG. 7 is a sectional view taken along a line III—III in FIG. 6. In FIGS. 5 and 6, the waist-circumferential direction is indicated by the arrow X, the longitudinal direction is indicated by the arrow Y and the leg-circumferential direction is indicated by the arrow Z (in FIG. 5 alone).

The article 1B is similar to the article 1A in many aspects. Specifically, the article 1B comprises a base sheet assembly 2 and a liquid-absorbent panel 3 attached to the inner side of the base sheet assembly 2 so as to define a waist-hole 11 and a pair of leg-holes 12. The article 1B is composed of front and rear waist regions 4, 6 opposed to each other and a crotch region 5 extending between these waist regions 4, 6. The panel 3 extends between the front and rear waist regions 4, 6 of the base sheet assembly 2 and has longitudinally opposite end zones 7 extending in the waist-circumferential direction in the front and rear waist regions 4, 6 of the base sheet assembly 2, respectively, and transversely opposite side zones 8 extending in the longitudinal direction between the front and rear waist regions 4, 6 of the base sheet assembly 2.

The article 1B is distinguished from the article 1A of FIG. 1 in a unique distribution of heat-sealing spots 33 at which an inner sheet 13 (first sheet) and an outer sheet 14 (second sheet) are joined to each other. Specifically, a plurality of the heat-sealing spots 33 are distributed in the region in which remaining portions 26, 27 of elastic elements 20, 21 lie so that the heat-sealing spots 33 may be located between each pair of the first elastic elements 20 adjacent to each other as well as between each pair of the second elastic elements 21 adjacent to each other. In addition, a plurality of heat-sealing spots 34 are distributed along the transversely opposite side zones 8 of the panel 3 extending in the front and rear waist regions 4, 6 so that these heat-sealing spots 34 may be located between each pair of the first elastic elements 20 adjacent to each other as well as between each pair of the second elastic elements 21 adjacent to each other. The inner and outer sheets 13, 14 constituting the base sheet assembly 2 are made of hydrophobic fibrous nonwoven fabric. At the heat-sealing spots 33, 34, the component fibers of the nonwoven fabric layers forming the inner and outer sheets 13, 14 are welded together.

Along a peripheral zone 11a of the waist-hole 11 defined by the end zones 7 in the front and rear waist regions 4, 6, respectively, the base sheet assembly 2 is provided with waist-surrounding elastic members 15 attached thereto in a stretched state. In the front and rear waist regions 4, 6, the base sheet assembly 2 is further provided between the waist-surrounding elastic member 15 and the leg-holes 12 with auxiliary elastic members 16 attached thereto and spaced apart from one another by given dimensions in the longitudinal direction. Along the peripheral zones 12a of the leg-holes 12 defined in the crotch region 5, the base sheet assembly 2 is provided with respective leg-surrounding elastic members 17 attached thereto in a stretched state. In the front and rear waist regions 4, 6, the base sheet assembly 2 is provided with indication sheets 18 each printed with the illustrated bear's head (indicator element 19).

The waist-surrounding elastic members 15 are interposed between the inner sheet 13 and the outer sheet 14 and attached to these sheets 13, 14 by means of a hot melt adhesive 35. The leg-surrounding elastic member 17 comprises third elastic elements 28 attached to the base sheet assembly 2 and the fourth elastic elements 29 attached to the panel 3. The third elastic elements 28 are interposed between the inner and outer sheets 13, 14 and attached to these sheets 13, 14 by means of a hot melt adhesive 39 intermittently applied to these sheets 13, 14, respectively. Each of the indication sheets 18 is interposed between the inner and outer sheets 13, 14 and has its outer surface attached to the inner surface of the outer sheet 14 by means of hot melt adhesive (not shown). As a stock material for this indication sheet 18, a breathable but liquid-impervious plastic film is used.

The auxiliary elastic members 16 include a plurality of first elastic elements 20 lying below the waist-surrounding elastic member 15 and a plurality of second elastic elements 21 lying below these first elastic elements 20. The first and second elastic elements 20, 21 are interposed between the inner sheet 13 and the outer sheet 14.

The first and second elastic elements 20, 21 respectively have opposite end portions 22, 23 extending in the vicinity of the lateral marginal zones 9 of the base sheet assembly 2, middle portions 24, 25 extending across the panel 3 and the remaining portions 26, 27 lying outside the opposite side zones 8 of the panel 3 so as to extend between the end portions 22, 23 and the middle portions 24, 25. The end portions 22, 23 of the first and second elastic elements 20, 21 are secured to the outer surface of the inner sheet 13 and the inner surface of the outer sheet 14. The middle portions 24 of the first elastic elements 20 are secured to the outer surface of the inner sheet 13 and the inner surface of the outer sheet 14. The remaining portions 26, 27 of the first and second elastic elements 20, 21 and the middle portions 25 of the second elastic elements 21 are not secured to these inner and outer sheets 13, 14 and let free from these sheets 13, 14.

The panel 3 comprises a liquid-pervious upper sheet 30 facing the wearer's body, a liquid-impervious lower sheet 31 facing away from the wearer's body and a liquid-absorbent core 32 interposed between these upper and lower sheets 30, 31. In the panel 3, an entire outer surface of the lower sheet 31 is joined to the inner surface of the inner sheet 13 by means of a hot melt adhesive applied intermittently to the inner sheet 13. The four elastic elements 29 are interposed between the upper and lower sheets 30, 31 and attached to the inner surfaces of these sheets 30, 31.

In the article 1B, the middle portions 24 of the first elastic elements 20 are secured to the inner and outer sheets 13, 14 in the front and rear waist regions 4, 6. Therefore, it is not likely that the first elastic elements 20 might shift in the longitudinal direction and these first elastic elements 20 might locally gather together in the front and rear waist regions 4, 6 even if movement of the wearer's waist or hip is transmitted to the first elastic elements 20. There is no anxiety that the middle portions 24 of the first elastic elements 20 might be separated off from the end zones 7 of the panel 3. Instead, the middle portions 24 of the first elastic elements 20 function to force the end zones 7 of the panel 3 against the wearer's waist or hip as the first elastic elements 20 contract inward in the waist-surrounding direction. In this way, there is no anxiety that the bodily discharge absorbing capacity of the panel 3 might be deteriorated in the vicinity of its end zones 7 lying in the front and rear waist regions 4, 6.

In the region in which the remaining portions 26, 27 of the elastic elements 20, 21 lie, the inner and outer sheets 13, 14 are joined to each other by means of a plurality of the heat-sealing spots 33. Such an arrangement ensures that the first and second elastic elements 20, 21 do not shift in the longitudinal direction in this region. In the article 1B, the first and second elastic elements 20, 21 contracting inward in the waist-circumferential direction function to press the entire area of the panel 3 against the wearer's waist and hip. Consequently, there is no anxiety that the bodily discharge absorbing capacity of the panel 3 lying in the front and rear waist regions 4, 6 might be deteriorated.

In the case of the article 1B, a plurality of the heat-sealing spots 34 are arranged along the side zones 8 of the panel 3 extending in the front and rear waist regions 4, 6. Such an arrangement reliably prevents the elastic elements 20, 21 from shifting in the longitudinal direction and thereby prevents these elastic elements 20, 21 from locally gathering together in the front and rear waist regions 4, 6 even if the movement from the side zones 8 of the panel 3 which are particularly deformable is transmitted to the first and second elastic elements 20, 21.

A stock material for the inner and outer sheets 13, 14 may be selected from the group consisting of a breathable but liquid-impervious plastic film, a composite nonwoven fabric comprising two or more hydrophobic fibrous nonwoven layers placed upon one another and a composite sheet comprising a hydrophobic fibrous nonwoven fabric and a breathable but liquid-impervious plastic film placed upon each other.

A stock material for the upper sheet 30 may be selected from the group consisting of a hydrophilic fibrous nonwoven fabric, a hydrophobic fibrous nonwoven fabric having a plurality of perforations and a plastic film having a plurality of fine perforations. A stock material for the lower sheet 31 may be selected from the group consisting of a hydrophobic fibrous nonwoven fabric, a breathable but liquid-impervious plastic film, a composite nonwoven fabric comprising two or more hydrophobic fibrous nonwoven fabric layers and a composite sheet comprising a hydrophobic fibrous nonwoven fabric and a breathable but liquid-impervious plastic film placed upon each other.

The nonwoven fabric may be selected from the group consisting of those obtained by spun lace-, needle punch-, melt blown-, thermal bond-, spun bond-, chemical bond- and air-through-processes. Component fibers of the nonwoven fabric may be selected from the group consisting of polyolefine-, polyester- and polyamide-based fibers and core-and-sheath type or side-by-side type conjugated fibers of polyethylene/polypropylene and polyethylene/polyester.

The core 32 comprises a mixture of fluff pulp and super-absorbent polymer particles or a mixture of fluff pulp, super-absorbent polymer particles and thermoplastic synthetic resin fibers each compressed to a given thickness. The core 32 is preferably entirely covered with a liquid-pervious sheet such as a tissue paper or a hydrophilic fibrous nonwoven fabric in order to prevent the core 32 from getting out of shape and to prevent the polymer particles from falling off therefrom. The polymer particles may be selected from the group consisting of starch-based polymer particles, cellulose-based polymer particles and synthetic polymer particles.

Joining the upper and lower sheets 30, 31, attaching the elastic elements 29 to the upper and lower sheets 30, 31, and attaching the core 32 to the upper and lower sheets 30, 31 may be carried out using hot melt adhesive or welding technique such as heat-sealing or sonic sealing technique. In both the article 1A and the article 1B, it is possible to attach the auxiliary elastic member 16 to at least the front waist region 4 and to eliminate the auxiliary elastic member 16 attached to the rear waist region 6.

The pull-on disposable wearing article according to the present invention is characterized in that the middle portions of the first elastic elements extending across the panel are attached to at least one of the first and second sheets. Such an arrangement is effective to prevent the first elastic elements from locally gathering together in the waist regions and/or to prevent the first elastic elements from forming a bundle which would locally tighten the wearer's waist and hip even if movement of the wearer's waist and hip is transmitted to the first elastic elements. Furthermore, there is no possibility that the middle portions of the first elastic elements might be separated off from the longitudinally opposite end zones of the panel and a contractile force of the first elastic elements can be utilized to press these end zones of the panel against the wearer's waist and hip. Correspondingly, the bodily discharge absorbing capacity can be fully utilized.

In the article according to the invention, the remaining portions of the first and second elastic elements as well as the middle portions of the second elastic elements are not secured to the first and second sheets. With an advantageous consequence, it is not likely that a plurality of gathers might be formed in the region of the base sheet assembly in which the remaining portions and the middle portions of the first and second elastic elements lie even if these elastic elements contract inward in the waist-circumferential direction. In this way, touch and appearance of the base sheet assembly can be improved.

In the case of the article provided, in the region in which the second elastic elements lie, with the indication sheets, there is no anxiety that a plurality of gathers might be formed not only in the base sheet assembly but also in the indication sheets. Thus, the indicator elements printed on the respective indication sheets are always clearly visible.

In the case of the article arranged so that the first and second sheets are joined together at a plurality of the heat-sealing spots provided in the region in which the remaining portions of the first and second elastic elements lie, there is no possibility that the first and second elastic elements might shift in the longitudinal direction in the above-mentioned region. In the article according to this invention, a contractile force of the first and second elastic elements can be utilized to press the entire area of the panel ling in the front and rear waist regions against the wearer's waist and hip and thereby the bodily discharge absorbing capacity of the panel lying in the front and rear waist regions can be fully utilized.

In the case of the article, a plurality of heat-sealing spots used to join the first and second sheets together are located also along the side zones of the panel extending in the front and rear waist regions, there is no anxiety that the first and second elastic elements might shift in the longitudinal direction and these elastic elements might locally gather together in the front and rear waist regions even if the movement from side zones of the panel which are particularly deformable is transmitted to the first and second elastic elements.

What is claimed is:

1. A pull-on disposable wearing article, comprising:
   a base sheet assembly which defines front and rear waist regions and a crotch region extending in a longitudinal direction of said article between said waist regions, wherein said front and rear waist regions defined by said base sheet assembly are connected to each other in vicinities of lateral marginal zones of said base sheet assembly to form a waist-hole and a pair of leg-holes;
   a liquid-absorbent panel which is attached to an inner side of said base sheet assembly so as to extend over said crotch region further into said front and rear waist regions;
   a waist-surrounding elastic member which extends in a waist-circumferential direction and is attached in a stretched state to said base sheet assembly along a peripheral edge of said waist-hole in said front and rear waist regions; and
   auxiliary elastic members which extend in said waist-circumferential direction and are attached in a stretched stated to said base sheet assembly in at least said front waist region and between said waist-surrounding elastic member and said leg-holes, so as to be spaced apart one from another at regular intervals in the longitudinal direction;
   wherein
   said base sheet assembly comprises a first sheet facing said panel and a second sheet facing away from said panel;
   said auxiliary elastic members comprise
      first elastic elements lying below said waist-surrounding elastic member and interposed between said first and second sheets, and
      second elastic elements lying below said first elastic elements and interposed between said first and second sheets;
   said first and second elastic elements respectively have
      longitudinally opposite end portions in vicinities of said lateral marginal zones of said base sheet assembly,
      middle portions underlying and extending across said panel, and
      remaining portions lying outside transversely opposite side edge zones of said panel and extending between and connecting respective said end portions and said middle portions; and
   said longitudinally opposite end portions of said first and second elastic elements and said middle portions of said first elastic elements are directly secured by adhesive to at least one of said first and second sheets, while said remaining portions of said first and second elastic elements and said middle portions of said second elastic elements are free from direct securement to both said first sheet and said second sheet.

2. The wearing article according to claim 1, further comprising indication sheets each having a given indicator element thereon, wherein said indication sheets are placed in regions in which said middle portions of said second elastic elements extend and wherein said indication sheets are secured to an inner surface of said second sheet.

3. The wearing article according to claim 1, further comprising heat-sealing spots which join said first and second sheets together and are distributed in regions in which said remaining portions of said first and second elastic elements lie, so that the individual heat-sealing spots are located between each pair of adjacent said first elastic elements as well as between each pair of adjacent said second elastic elements.

4. The wearing article according to claim 3, wherein said heat-sealing spots are arranged along said transversely opposite side zones of said panel in said front and rear waist regions.

5. The wearing article according to claim 1, further comprising leg-surrounding elastic members which are attached in a stretched state to said base sheet assembly along peripheral edges of respective said leg-holes.

6. The wearing article according to claim 1, wherein said panel comprises a liquid-pervious upper sheet adapted to face a wearer's body, a liquid-impervious lower sheet adapted to face away from the wearer's body, and a liquid-absorbent core interposed between said upper and lower sheets.

7. A pull-on disposable wearing article, comprising:
a base sheet assembly which defines front and rear waist regions and a crotch region extending in a longitudinal direction of said article between said waist regions, wherein said front and rear waist regions defined by said base sheet assembly are connected to each other in vicinities of lateral marginal zones of said base sheet assembly to form a waist-hole and a pair of leg-holes;
a liquid-absorbent panel which is attached to an inner side of said base sheet assembly so as to extend over said crotch region further into said front and rear waist regions;
a waist-surrounding elastic member which extends in a waist-circumferential direction and is attached in a stretched state to said base sheet assembly along a peripheral edge of said waist-hole in said front and rear waist regions; and auxiliary elastic members which extend in said waist-circumferential direction and are attached in a stretched stated to said base sheet assembly in at least said front waist region and between said waist-surrounding elastic member and said leg-holes, so as to be spaced apart one from another at regular intervals in the longitudinal direction;
wherein
said base sheet assembly comprises a first sheet facing said panel and a second sheet facing away from said panel;
said auxiliary elastic members comprise
first elastic elements lying below said waist-surrounding elastic member and interposed between said first and second sheets, and
second elastic elements lying below said first elastic elements and interposed between said first and second sheets;
said first and second elastic elements respectively have
longitudinally opposite end portions extending in vicinities of said lateral marginal zones of said base sheet assembly,
middle portions extending across said panel, and
remaining portions lying outside transversely opposite side edge zones of said panel and extending between respective said end portions and said middle portions;
said longitudinally opposite end portions of said first and second elastic elements and said middle portions of said first elastic elements are directly secured to at least one of said first and second sheets, while said remaining portions of said first and second elastic elements and said middle portions of said second elastic elements are free from direct securement to both said first sheet and said second sheet;
said first and second sheets are directly attached to each other at a plurality of bonding spots distributed in regions corresponding to said remaining portions of said first and second elastic elements; and
said bonding spots are presented between every pair of adjacent said auxiliary elastic members so as to prevent said adjacent auxiliary elastic members from forming a bundle with each other.

8. The article of claim 7, wherein said first and second sheets are free of direct attachment to one another in regions corresponding to the middle portions of said first and second elastic members.

* * * * *